United States Patent [19]

Kang

[11] Patent Number: 5,969,185
[45] Date of Patent: Oct. 19, 1999

[54] PROCESS FOR MAKING PHENOLIC KETONES

[75] Inventor: Sang I. Kang, Ft. Washington, Pa.

[73] Assignee: Henkel Corporation, Gulph Mills, Pa.

[21] Appl. No.: 09/103,692

[22] Filed: Jun. 24, 1998

Related U.S. Application Data

[60] Provisional application No. 60/052,512, Jul. 14, 1997.

[51] Int. Cl.⁶ .................................................. C07C 249/08

[52] U.S. Cl. ............................................ 564/259; 568/315

[58] Field of Search .............................. 568/315; 564/259

[56] References Cited

U.S. PATENT DOCUMENTS

| | | | |
|---|---|---|---|
| 3,665,013 | 5/1972 | Fitzmaurice et al. | 260/343.2 |
| 4,231,967 | 11/1980 | Atsuda et al. | 568/433 |
| 4,638,096 | 1/1987 | Virnig | 568/315 |
| 5,502,254 | 3/1996 | Levin | 564/259 |

*Primary Examiner*—James H. Reamer
*Attorney, Agent, or Firm*—Ernest G. Szoke; Wayne C. Jaeschke; Henry E. Millson

[57] ABSTRACT

A process for making a phenolic ketone involving reacting a metal aryloxide with an aliphatic aldehyde having from at least 2 to about 25 carbon atoms.

21 Claims, No Drawings

PROCESS FOR MAKING PHENOLIC KETONES

CROSS-REFERENCE TO RELATED APPLICATION

This application claims priority from U.S. provisional application Ser. No. 60/052,512, filed Jul. 14, 1997, the disclosure of which is incorporated herein by reference.

BACKGROUND OF THE INVENTION

1. Field of the Invention

The present invention generally relates to a process for making phenolic ketones. More particularly, a process is provided for making phenolic ketones, which may be used as precursors to the synthesis of hydroxyaryl ketoximes, used as extractants for the recovery of metals from aqueous solutions.

2. Background of the Invention

The starting material for solvent extraction processing of copper is an aqueous leach solution obtained from a body of ore which contains a mixture of metal in addition to copper. The leaching medium dissolves salts of copper and other metals as it trickles through the ore, to provide an aqueous solution of the mixture of metal values. The metal values are usually leached with sulfuric acid medium, providing an acidic aqueous solution, but can also be leached by ammonia to provide a basic aqueous solution.

The aqueous solution is mixed in tanks with an extraction reagent which is dissolved in an organic solvent, e.g., a kerosene. The reagent includes an extractant chemical which selectively forms metal-extractant complex with the copper ions in preference to ions of other metals. The step of forming the complex is called the extraction or loading stage of the solvent extraction process.

The outlet of the mixer continuously feeds to a large settling tank, where the organic solvent (organic phase), now containing the copper-extractant complex in solution, is separated from the depleted aqueous solution (aqueous phase). This part of the process is called phase separation. Usually, the process of extraction is repeated through two or more mixer/settler stages, in order to more completely extract the desired metal.

After extraction, the depleted aqueous feedstock (raffinate) is either discharged or recirculated to the ore body for further leaching. The loaded organic phase containing the dissolved copper-extractant complex is fed to another set of mixer tanks, where it is mixed with an aqueous strip solution of concentrated sulfuric acid. The highly acid strip solution breaks apart the copper-extractant complex and permits the purified and concentrated copper to pass to the strip aqueous phase. As in the extraction process described above, the mixture is fed to another settler tank for phase separation. This process of breaking the copper-extractant complex is called the stripping stage, and the stripping operation is repeated through two or more mixer-settler stages to more completely strip the copper from the organic phase.

From the stripping settler tank, the regenerated stripped organic phase is recycled to the extraction mixers to begin extraction again, and the strip aqueous phase is customarily fed to an electrowinning tankhouse, where the copper metal values are deposited on plates by a process of electrodeposition. After electrowinning the copper values from the aqueous solution, the solution, known as spent electrolyte, is returned to the stripping mixers to begin stripping again.

While many reagent formulations have been proposed for use in recovery of copper by solvent extraction, the present invention is specifically directed to the hydroxyaryl ketoxime reagents. Hydroxyaryl ketoximes are typically derived by reacting a phenolic ketone with a hydroxylamine derivative. The most common method used for deriving the phenolic ketones is through the conversion of an alkylphenyl acetate to a phenolic ketone by way of a Fries rearrangement using aluminum chloride as the catalyst.

A significant disadvantage associated with the use of this type of process to make phenolic ketones stems from the large amounts of aluminum chloride required to make the phenolic ketones and, more particularly, the substantial amounts of aluminum chloride waste being generated thereby. Moreover, a two-pot conversion is required, i.e., preparation of the ester intermediate in one reactor, followed by transference of the ester intermediate to a second pot, i.e., second reactor, to perform the Fries rearrangement.

As was noted previously, hydroxyaryl ketoximes are derived by reacting a phenolic ketone with a hydroxylamine derivative. Thus, in order to form the desired ketoximes, another process is required, i.e., formation of the phenolic ketones in two pots, followed by transference to a third pot so that they can be reacted with the hydroxylamine derivative.

SUMMARY OF THE INVENTION

The present invention is directed to a process for making phenolic ketones corresponding to formula I:

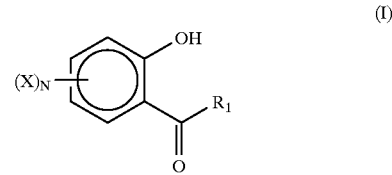

wherein $R_1$ is a $C_1$ to $C_{24}$ alkyl group, X is a hydrogen or halogen atom, or an alkyl, cycloalkyl, aralkyl, aryl, alkaryl, alkoxy, aryloxy, acyl or hydroxy group, n is an integer from 1 to 4, and $R_1$ and X have a combined total of from about 3 to about 25 carbon atoms. The process involves reacting a metal aryloxide with an aliphatic aldehyde having from at least 2 to about 25 carbon atoms to form the phenolic ketone of formula 1. The metal aryloxide is derived by reacting an alkoxide or hydride of Group IA, IIA, IIIA or IVB of the Periodic Table with substituted phenols.

The present invention is also directed to a process for making phenolic ketoximes corresponding to formula II:

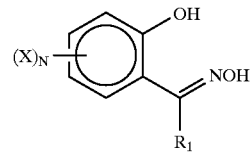

wherein $R_1$ is a $C_1$ to $C_{24}$ alkyl group, X is a hydrogen or halogen atom, or an alkyl, cycloalkyl, aralkyl, aryl, alkaryl, alkoxy, aryloxy, acyl, hydroximinoacyl or hydroxyl group, n is an integer from 1 to 4, and $R_1$ and X have a combined total of from about 3 to about 25 carbon atoms, involving the steps of:

(a) providing a phenolic ketone formed by reacting a metal aryloxide with an aliphatic aldehyde having from at least 2 to about 25 carbon atoms;

(b) providing a hydroxylamine derivative; and (c) reacting the phenolic ketone of (a) with the hydroxylamine derivative of (b).

DESCRIPTION OF THE INVENTION

Other than in the operating examples, or where otherwise indicated, all numbers expressing quantities of ingredient or reaction conditions, are to be understood as being modified in all instances by the term "about".

The present invention relates to the formation of phenolic ketones corresponding to formula I:

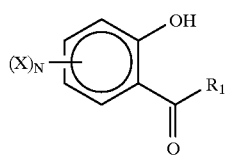

(I)

wherein $R_1$ is a $C_1$ to $C_{24}$ alkyl group, X is a hydrogen or halogen atom, or an alkyl, cycloalkyl, aralkyl, aryl, alkaryl, alkoxy, aryloxy, acyl or hydroxy group, n is an integer from 1 to 4, and $R_1$ and X have a combined total of from about 3 to about 25 carbon atoms, obtained by reacting a metal aryloxide with an aliphatic aldehyde having from at least 2 to about 25 carbon atoms.

Metal aryloxides which may be used in the process of the invention may be obtained by conventional methods. It should be noted that Group IA, IIA, IIIA and IVB aryloxides are known to contain aryloxy groups for each metal atom, i.e., one mole of Group IA, IIA, IIIA and IVB aryloxides contains two, three and four aryloxy equivalents, respectively. Especially useful metal aryloxides include aluminum, magnesium, titanium or zirconium aryloxides wherein the phenoxy residues may be unsubstituted or may be substituted in any or all of the positions, other than both the 2- and 6-positions, by substituents which do not interfere with the course of the reaction and which preferably are electron-repelling or weakly electron-attracting.

Particularly preferred metal aryloxides are those derived from phenols corresponding to formula III:

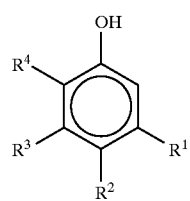

(III)

wherein each of $R_1$, $R_2$, $R_3$ and $R_4$, independently, represents a hydrogen or halogen atoms or an alkyl, cycloalkyl, aralkyl, aryl, alkaryl, alkoxy, aryloxy, acyl or hydroxy group.

Particular mention may also be made of metal aryloxides derived from phenols corresponding to formula IV:

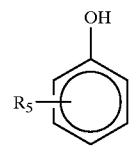

(IV)

wherein $R_5$ represents hydrogen or a $C_{1-22}$ alkyl radical, especially a branched heptyl, octyl, nonyl or dodecyl radical in the para position. Other preferred phenols include ortho, meta and para cresol; ortho, meta and para chlorophenol; ortho, meta and para methoxyphenol; meta and para hydroxyacetophenone, and resorcinol, catechol and hydroquinone.

The above-described metal aryloxides are reacted with an aliphatic aldehyde having from at least 2 to about 25 carbon atoms. A particularly preferred aliphatic aldehyde for use in the process of the present invention is acetaldehyde.

According to one embodiment of the present invention, there is provided a process for making phenolic ketones involving reacting a metal aryloxide, preferably, an aluminum aryloxide, and most preferably an aluminum paraalkylphenoxide, with an aliphatic aldehyde, preferably acetaldehyde. These two reactants are employed at a molar ratio of aluminum aryloxide:aliphatic aldehyde of from about 1:2 to about 1:40, preferably from about 1:2 to about 1:20, more preferably from about 1:2 to about 1:10, and most preferably from about 1:2.5 to about 1:5.

Another critical variable relating to this process relates to the temperature and pressure at which the metal aryloxide and aliphatic aldehyde are reacted. The reaction will typically be carried out at a pressure of from about atmospheric pressure to about 300 psi, and a temperature of from at least 20° C. up to about 250° C., and preferably from about 50 to about 150° C.

Two advantages associated with the process of the present invention is that it allows phenolic ketones to be made in a one pot conversion, while eliminating the need for engaging in a Fries rearrangement. In one embodiment of the invention, the phenolic ketone is isolated by acidifying the reaction mixture and washing out the resulting inorganic metal salt. The resulting crude phenolic ketone may then be purified by conventional techniques such as, for example, distillation.

In an alternative embodiment of the invention, once the phenolic ketone is formed, it can then be used to synthesize, in the same pot, a phenolic ketoxime corresponding to formula 11:

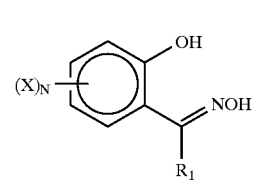

(II)

wherein $R_1$ is a $C_1$ to $C_{24}$ alkyl group, X is a hydrogen or halogen atom, or an alkyl, cycloalkyl, aralkyl, aryl, alkaryl, alkoxy, aryloxy, acyl, hydroximinoacyl or hydroxyl group, n is an integer from 1 to 4 and $R_1$ and X have a combined total of from about 3 to about 25 carbon atoms.

The phenolic ketone of formula I is reacted with a source of hydroxylamine to form the desired phenolic ketoxime. Suitable sources of hydroxylamine include, but are not limited to, hydroxylammonium sulfate, hydroxylammonium bisulfate and hydroxylammonium chloride.

These two reactants are typically employed at a molar ratio of phenolic ketone:hydroxylamine of from about 1:1 to about 1:2, and preferably about 1:1.1. The reaction is typically carried out at atmospheric pressure, and a temperature of from at about 20° C. to about 100° C., and preferably from about 60 to about 70° C.

The advantage associated with this aspect of the process is that it allows both the phenolic ketone precursor and the phenolic ketoxime final product to be made in a one pot conversion. In other words, the phenolic ketone is made in a single reactor, per the process as described above. Once the phenolic ketone is formed, the hydroxylamine can then be added to it, in the same reactor, in order to make the desired phenolic ketoxime final product.

The phenolic ketoxime, thus formed, can then be used in a variety of applications such as, for example, solvent extraction processes for the recovery of metals.

The present invention will be better understood from the examples which follow, all of which are intended for illustrative purposes only, and are not meant to unduly limit the scope of the invention in any way.

EXAMPLES

Example 1

Preparation of 2-Hydroxy-5-nonylacetophenone (HNA)

4-Nonylphenol (22 g, 100 mmol) and aluminum isopropoxide (7.15 g, 35 mmol) were mixed in toluene (100 mL) and isopropanol(10 mL) in a four-necked round bottomed flask equipped with a condenser, a mechanical stirrer, and a thermometer. The mixture was heated to 100–115° C. while removing the isopropanol and some toluene. To the cooled mixture was added, at 45–50° C., acetaldehyde (13.4 g, 305 mmol) for a period of 50 min maintaining at the same temperature. After the addition of the acetaldehyde, the mixture was stirred for 60 min, cooled to ambient temperature, and then treated with 150 g/l sulfuric acid (100 mL) and heptane (100 mL) in a separatory funnel. The organic layer was then separated and dried with sodium sulfate. Removal of the solvents followed by GC-IR analysis of the residue showed a 14% yield of HNA.

As was noted above, one of the significant advantages of the process of the present invention is that it enables both the phenolic ketone precursor and the phenolic ketoxime final product to be made in a one pot conversion, i.e., in a single reactor.

Example 2

Preparation of 2-Hydroxy-5-nonylacetophenone (HNA)

4-Nonylphenol (22 g, 100 mmol) and zirconium n-butoxide (80% in n-butanol, 12.61 g, 26.3 mmol) were mixed in xylenes (100 mL) in a four-necked round bottomed flask equipped with a condenser, a mechanical stirrer, and a thermometer. The mixture was heated to 120–140 ° C. while removing the n-butanol and some xylenes. To the cooled mixture was added, at 60–70° C., acetaldehyde (13.4 g, 305 mmol) for a period of 50 min maintaining at the same temperature. After the addition of the acetaldehyde, the mixture was stirred for 50 min, cooled to ambient temperature, and then treated with 250 g/l sulfuric acid (100 mL) and heptane (100 mL) in a separatory funnel. The organic layer was then separated and dried with sodium sulfate. Removal of the solvents followed by GC-IR analysis of the residue showed a 10.3% yield of HNA.

Example 3

Preparation of 2-Hydroxy-5-nonylisobutyrophenone (HNI)

4-Nonylphenol (22.3 g, 101.4 mmol) and magnesium methoxide (60 mL of 9.5% in methanol, 53.8 mmol) were mixed in toluene (100 mL) in a four-necked round bottomed flask equipped with a condenser, a mechanical stirrer, and a thermometer. The mixture was heated to 95–100° C. while removing the methanol and some toluene. To the cooled mixture was added, at 60° C., isobutyraldehyde (63 g, 874 mmol) for a period of 60 to 75 min. The temperature was then raised and maintained at between 95 and 105° C. for about 1 hour. The mixture was then cooled to ambient temperature and treated with 150 g/l sulfuric acid (100 mL) and heptane (100 mL) in a separatory funnel. The organic layer was then separated and dried with sodium sulfate. Removal of the solvents followed by GC-IR analysis of the residue showed a 28% yield of 2-hydroxy-5-nonylisobutyrophenone.

Example 4

Preparation of 2-Hydroxy-5-nonylacetophenone (HNA)

4-Nonylphenol (22 g, 100 mmol) and aluminum isopropoxide (7.15 g, 35 mmol) were mixed in toluene (100 mL)and isopropanol(10 mL) in a four-necked round bottomed flask equipped with a condenser, a mechanical stirrer, and a thermometer. The mixture was heated to 100–115° C. while removing the isopropanol and some toluene. To the cooled mixture was added, at 45–50° C., acetaldehyde (13.4 g, 305 mmol) for a period of 50 min maintaining at the same temperature. After the addition of the acetaldehyde, the mixture was stirred for 60 min, cooled to ambient temperature, and then treated with 150 g/l sulfuric acid (100 mL) and heptane (100 mL) in a separatory funnel. The organic layer was then separated and dried with sodium sulfate. Removal of the solvents followed by GC-IR analysis of the residue showed a 14% yield of HNA.

Example 5

Preparation of 2-Hydroxy-5-nonylacetophenone (HNA)

4-Nonylphenol (22 g, 100 mmol) and zirconium n-butoxide (80% in n-butanol, 12.61 g, 26.3 mmol) were mixed in xylenes (100 mL) in a four-necked round bottomed flask equipped with a condenser, a mechanical stirrer, and a thermometer. The mixture was heated to 120–140° C. while removing the n-butanol and some xylenes. To the cooled mixture was added, at 60–70° C., acetaldehyde (13.4 g, 305 mmol) for a period of 50 min maintaining at the same temperature. After the addition of the acetaldehyde, the mixture was stirred for 50 min, cooled to ambient temperature, and then treated with 250 g/l sulfuric acid (100 mL) and heptane (100 mL) in a separatory funnel. The organic layer was then separated and dried with sodium sulfate. Removal of the solvents followed by GC-IR analysis of the residue showed a 10.3% yield of HNA.

Example 6

Preparation of 2-Hydroxy-5-nonylisobutyrophenoxime (HNIO)

4-Nonylphenol (22.3 g, 101.4 mmol) and magnesium methoxide (60 mL of 9.5% in methanol, 53.8 mmol) are mixed in toluene (100 mL) in a four-necked round bottomed flask equipped with a condenser, a mechanical stirrer, and a thermometer. The mixture is then heated to from about 95–100° C. while removing the methanol and some toluene. To the cooled mixture, isobutyraldehyde (63 g, 874 mmol) are added for a period of from about 60 to about 75 min, at 60° C. The temperature is then raised to, and maintained between 95 and 105° C. for 1 h, after which it is cooled to about 75° C. To the mixture is added hydroxylamine sulfate (8.2 g, 50 mmol) dissolved in water (50 mL) for about 5 min. The resulting biphasic solution is vigorously stirred for about 2 h at 75° C., and then further treated with 150 g/l sulfuric acid (100 mL) at 55° C. for 30 min. The contents are then transferred into a separatory funnel, after being cooled to ambient temperature. The organic layer is then separated, and the aqueous phase washed with toluene (100 mL). The combined organic layers are then washed with water (100 mL×3) and dried over anhydrous sodium sulfate. Removal of the organic solvents will yield 2-hydroxy-5-nonylisobutyrophenoxime (HNIO).

What is claimed is:

1. A process for making phenolic ketones corresponding to formula I:

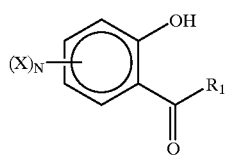

(I)

wherein $R_1$ is a $C_1$ to $C_{24}$ alkyl group, X is a hydrogen or halogen atom, or an alkyl, cycloalkyl, aralkyl, aryl, alkaryl, alkoxy, aryloxy, acyl or hydroxy group, n is an integer from 1 to 4, and $R_1$ and X have a combined total of from about 3 to about 25 carbon atoms comprising:
   (a) providing a metal aryloxide wherein the metal is a metal selected from the group consisting of metals from Groups IA, IIA, IIIA, and IVB of the periodic table;
   (b) providing an aliphatic aldehyde having from at least 2 to about 25 carbon atoms; and
   (c) reacting the metal aryloxide with the aliphatic aldehyde to form a phenolic ketone, wherein step (c) is carried out at a temperature of from about 20 to about 250° C. and at a pressure of from atmospheric to about 300 psi.

2. The process of claim 1 wherein the metal aryloxide is selected from the group consisting of an aluminum aryloxide, a magnesium aryloxide, a titanium aryloxide and a zirconium aryloxide.

3. The process of claim 1 wherein the metal aryloxide corresponds to a metal aryloxide of a phenol of formula III:

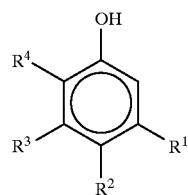

(III)

wherein each of $R_1$, $R_2$, $R_3$ and $R_4$, independently, represents a hydrogen or halogen atoms or an alkyl, cycloalkyl, aralkyl, aryl, alkaryl, alkoxy, aryloxy, acyl or hydroxy group.

4. The process of claim 1 wherein the aliphatic aldehyde is selected from the group consisting of acetaldehyde, propionaldehyde, n-butanal, isobutyraldehyde and 2-ethylhexanal.

5. The process of claim 1 wherein the metal aryloxide and aliphatic aldehyde are reacted at a molar ratio ranging from about 1:2 to about 1:40.

6. A process for making a phenolic ketoxime corresponding to formula II:

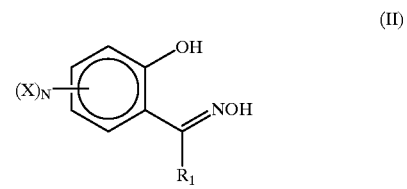

(II)

wherein $R_1$ is a $C_1$ to $C_{24}$ alkyl group, X is a hydrogen or halogen atom, or an alkyl, cycloalkyl, aralkyl, aryl, alkaryl, alkoxy, aryloxy, acyl, hydroximinoacyl or hydroxyl group, n is an integer from 1 to 4, and $R_1$ and X have a combined total of from about 3 to about 25 carbon atoms, comprising:
   (a) providing a metal aryloxide;
   (b) providing an aliphatic aldehyde;
   (c) reacting the metal aryloxide with the aliphatic aldehyde to form a phenolic ketone;
   (d) providing a source of hydroxylamine; and
   (e) reacting the phenolic ketone with the hydroxylamine to form the phenolic ketoxime; wherein step (c) is carried out at a temperature of from about 20 to about 250° C. and at a pressure of from atmospheric to about 300 psi, step (e) is carried out at a temperature of from about 20 to about 100° C., and the metal in the metal aryloxide in (a) is a metal selected from the group consisting of metals from Groups IA, IIA, IIIA, and IVB of the periodic table.

7. The process of claim 6 wherein the metal aryloxide is selected from the group consisting of an aluminum aryloxide, a magnesium aryloxide, a titanium aryloxide and a zirconium aryloxide.

8. The process of claim 6 wherein the metal aryloxide corresponds to a metal aryloxide of a phenol of formula III:

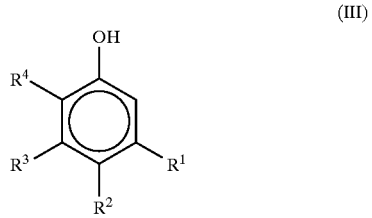

(III)

wherein each of $R_1$, $R_2$, $R_3$ and $R_4$, independently, represents a hydrogen or halogen atoms or an alkyl, cycloalkyl, aralkyl, aryl, alkaryl, alkoxy, aryloxy, acyl or hydroxy group.

9. The process of claim 6 wherein the aliphatic aldehyde is selected from the group consisting of acetaldehyde, propionaldehyde, n-butanal, isobutyraldehyde and 2-ethylhexanal.

10. The process of claim 6 wherein the metal aryloxide and aliphatic aldehyde are reacted at a molar ratio ranging from about 1:2 to about 1:40.

11. The process of claim 6 wherein the source of hydroxylamine is selected from the group consisting of hydroxyammonium sulfate, hydroxyammonium bisulfate and hydroxyammonium chloride.

12. The process of claim 6 wherein the phenolic ketone and source of hydroxyamine are reacted at a molar ratio of from about 1:1 to about 1:2.

13. The process of claim 12 wherein the phenolic ketone and source of hydroxyamine are reacted at a molar ratio of about 1:1.1.

14. The process of claim 6 wherein both the phenolic ketone and the phenolic ketoxime are both formed in a single reaction vessel.

15. The process of claim 1 wherein the metal aryloxide in (a) is an aluminum paraalkylphenoxide and the aliphatic aldehyde in (b) is acetaldehyde.

16. The process of claim 15 wherein the molar ratio of aluminum paraalkylphenoxide to acaetaldehyde is from about 1:2.5 to about 1:5.

17. The process of claim 11 wherein in (a) the metal aryloxide is aluminum paraalkylphenoxide; the aliphatic aldehyde in (b) is acetaldehyde; and the source of hydroxylamine in (d) is a hydroxylammonium sulfate.

18. The process of claim 17 wherein the molar ratio of aluminum paraalkylphenoxide to acetaldehyde is from about 1:2.5 to about 1:5.

19. The process of claim 18 wherein in step (e) the molar ratio of phenolic ketone to hydroxylammonium sulfate is about 1:1 to about 1:2.

20. The process of claim 1 wherein the metal aryloxide is a metal aryloxide of the phenol of formula IV:

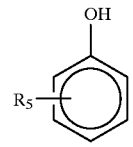

(IV)

wherein $R_5$ is hydrogen or a $C_{1-22}$ alkyl group.

21. The process of claim 6 wherein the metal aryloxide is a metal aryloxide of a phenol of formula IV:

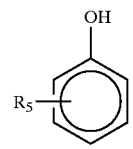

(IV)

wherein $R_5$ is hydrogen or a $C_{1-22}$ alkyl group.

* * * * *